(12) United States Patent
Zhang et al.

(10) Patent No.: US 11,093,820 B2
(45) Date of Patent: Aug. 17, 2021

(54) IMAGE ANALYSIS USING DEVIATION FROM NORMAL DATA

(71) Applicant: General Electric Company, Schenectady, NY (US)

(72) Inventors: Min Zhang, San Ramon, CA (US); Gopal Biligeri Avinash, San Ramon, CA (US)

(73) Assignee: General Electric Company, Schenectady, NY (US)

(*) Notice: Subject to any disclaimer, the term of this patent is extended or adjusted under 35 U.S.C. 154(b) by 21 days.

(21) Appl. No.: 15/855,033

(22) Filed: Dec. 27, 2017

(65) Prior Publication Data
US 2019/0122364 A1 Apr. 25, 2019

Related U.S. Application Data

(60) Provisional application No. 62/574,333, filed on Oct. 19, 2017.

(51) Int. Cl.
*G06N 3/04* (2006.01)
*G06N 3/08* (2006.01)
(Continued)

(52) U.S. Cl.
CPC ......... *G06N 3/0454* (2013.01); *G06K 9/6267* (2013.01); *G06N 3/08* (2013.01);
(Continued)

(58) Field of Classification Search
CPC ......... G06T 7/0012; G06T 2207/10072; G06T 2207/20081; G06T 2207/20084;
(Continued)

(56) References Cited

U.S. PATENT DOCUMENTS 5,769,074 A 6/1998 Barnhill et al.
8,064,660 B2 * 11/2011 Leow .................. G03B 42/02
382/128
(Continued)

FOREIGN PATENT DOCUMENTS

CA 2972183 A1 6/2017
CN 106446895 A 2/2017
(Continued)

OTHER PUBLICATIONS

Gousias et al. "Atlas selection strategy for automatic segmentation of pediatric brain MRIs into 83 ROIs." 2010 IEEE International Conference on Imaging Systems and Techniques. IEEE, 2010. (Year: 2010).*

(Continued)

*Primary Examiner* — Katrina R Fujita
(74) *Attorney, Agent, or Firm* — Amin, Turocy & Watson, LLP

(57) ABSTRACT

Systems and techniques for facilitating image analysis using deviation from normal data are presented. In one example, a system generates atlas map data indicative of an atlas map that includes a first portion of patient image data from a plurality of reference patients and a second portion of the patient image data from a plurality of target patients. The first portion of the patient image data is matched to a corresponding age group for a set of patient identities associated with the first portion of the patient image data. The system also generates deviation map data that represents an amount of deviation for the second portion of the patient image data compared to the first portion of the patient image data. Furthermore, the system trains a neural network based on the deviation map data to determine one or more clinical conditions.

20 Claims, 10 Drawing Sheets

(51) Int. Cl.
*G16H 30/40* (2018.01)
*G06N 20/20* (2019.01)
*G06K 9/62* (2006.01)
*G06T 7/00* (2017.01)

(52) U.S. Cl.
CPC .......... *G06N 20/20* (2019.01); *G06T 7/0012* (2013.01); *G16H 30/40* (2018.01); *G06K 2209/05* (2013.01); *G06T 2207/20081* (2013.01); *G06T 2207/20084* (2013.01)

(58) Field of Classification Search
CPC .......... G06T 2207/30016; G16H 30/40; G16H 50/20; G16H 50/50; G06N 3/0454; G06N 3/08; G06N 20/20; G06K 9/6255; G06K 9/6267; G06K 9/6273; G06K 2209/05
See application file for complete search history.

(56) References Cited

U.S. PATENT DOCUMENTS

| | | | |
|---|---|---|---|
| 9,589,374 | B1 | 3/2017 | Gao et al. |
| 9,607,373 | B2 * | 3/2017 | Buisseret ............... G06T 7/0012 |
| 10,140,544 | B1 | 11/2018 | Zhao et al. |
| 10,192,640 | B2 | 1/2019 | Itu et al. |
| 10,460,447 | B2 | 10/2019 | Song et al. |
| 10,650,929 | B1 | 5/2020 | Beck et al. |
| 2003/0194124 | A1 | 10/2003 | Suzuki et al. |
| 2009/0082637 | A1 | 3/2009 | Galperin |
| 2012/0051608 | A1 | 3/2012 | Avinash et al. |
| 2012/0070044 | A1 | 3/2012 | Avinash et al. |
| 2016/0300120 | A1 | 10/2016 | Hass et al. |
| 2017/0024641 | A1 | 1/2017 | Wierzynski |
| 2017/0039708 | A1 * | 2/2017 | Henry ................... A61B 5/055 |
| 2017/0185871 | A1 | 6/2017 | Zhang et al. |
| 2017/0200260 | A1 | 7/2017 | Bhaskar et al. |
| 2017/0213339 | A1 | 7/2017 | Hibbard et al. |
| 2017/0270653 | A1 | 9/2017 | Garnavi et al. |
| 2017/0287134 | A1 | 10/2017 | Abedini et al. |
| 2018/0033144 | A1 | 2/2018 | Risman et al. |
| 2018/0084988 | A1 | 3/2018 | Chakravorty et al. |
| 2018/0116620 | A1 | 5/2018 | Chen et al. |
| 2018/0247195 | A1 | 8/2018 | Kumar et al. |
| 2018/0253531 | A1 | 9/2018 | Sharma et al. |
| 2018/0263585 | A1 | 9/2018 | Weiss et al. |
| 2018/0315193 | A1 | 11/2018 | Paschalakis et al. |
| 2018/0350066 | A1 | 12/2018 | Zuyev et al. |
| 2018/0360313 | A1 | 12/2018 | Zhang |
| 2019/0005684 | A1 | 1/2019 | De Fauw et al. |
| 2019/0030371 | A1 | 1/2019 | Han |
| 2019/0050981 | A1 | 2/2019 | Song et al. |
| 2019/0057515 | A1 | 2/2019 | Teixeira et al. |
| 2019/0065897 | A1 | 2/2019 | Li |
| 2019/0080456 | A1 | 3/2019 | Song et al. |
| 2019/0122075 | A1 | 4/2019 | Zhang et al. |
| 2019/0122360 | A1 | 4/2019 | Zhang et al. |
| 2019/0122364 | A1 | 4/2019 | Zhang et al. |
| 2019/0148021 | A1 * | 5/2019 | Styner ................. A61B 5/7267 705/2 |
| 2020/0082930 | A1 | 3/2020 | De Francesco et al. |

FOREIGN PATENT DOCUMENTS

| | | |
|---|---|---|
| CN | 106952338 A | 7/2017 |
| CN | 107067396 A | 8/2017 |
| CN | 107256396 A | 10/2017 |
| CN | 107846012 A | 3/2018 |
| WO | 2010/005969 A2 | 1/2010 |

OTHER PUBLICATIONS

Gousias et al. "Automatic segmentation of pediatric brain MRIs using a maximum probability pediatric atlas." 2012 IEEE International Conference on Imaging Systems and Techniques Proceedings. IEEE, 2012. (Year: 2012).*

Kawahara et al. "BrainNetCNN: Convolutional neural networks for brain networks; towards predicting neurodevelopment." NeuroImage 146 (Feb. 2017): 1038-1049. (Year: 2017).*

Metzger, Andrew. "An automated tissue classification pipeline for magnetic resonance images of infant brains using age-specific atlases and level set segmentation." (2016). (Year: 2016).*

Sanchez et al. "Neurodevelopmental MRI brain templates for children from 2 weeks to 4 years of age." Developmental psychobiology 54.1 (2012): 77-91. (Year: 2012).*

Sethi et al. "Deep neural networks for segmentation of basal ganglia sub-structures in brain MR images." Proceedings of the Tenth Indian Conference on Computer Vision, Graphics and Image Processing. 2016. (Year: 2016).*

Hwang et al., "Self-Transfer Learning for Fully Weakly Supervised Object Localization," arXiv:1602.01625v1 [cs.CV], Feb. 4, 2016, 9 pages.

Dubost et al., "GP-Unet: Lesion Detection from Weak Labels with a 3D Regression Network", International Conference on Medical Image Computing and Computer-Assisted Intervention, MICCAI, Sep. 4, 2017, pp. 214-221.

Oktay et al., "Anatomically Constrained Neural Networks (ACNN): Application to Cardiac Image Enhancement and Segmentation", IEEE Transactions on Medical Imaging, vol. 37, No. 2, Aug. 29, 2017, pp. 1-13.

Payer et al., "Multi-Label Whole Heart Segmentation Using CNNs and Anatomical Label Configurations", Institute for Computer Graphics and Vision, vol. 10663, 2017, pp. 1-8.

Rohe et al., "Automatic Multi-Atlas Segmentation of Myocardium with SVF-Net", Statistical Atlases and Computational Models of the Heart (STACOM), Aug. 18, 2017, 9 pages.

Wang et al., "ChestX-ray8: Hospital-scale Chest X-ray Database and Benchmarks on Weakly-Supervised Classification and Localization of Common Thorax Diseases", IEEE Conference on Computer Vision and Pattern Recognition (CVPR), Jul. 21, 2017, pp. 3462-3471.

International Search Report and Written Opinion received for PCT Application Serial No. PCT/US2018/018902 dated Jul. 2, 2018, 10 pages.

Non-Final Office Action received for U.S. Appl. No. 15/792,698 dated Mar. 11, 2019, 44 pages.

International Search Report and Written Opinion received for PCT Application Serial No. PCT/US2018/031779 dated Jul. 16, 2018, 9 pages.

Shin et al., "Deep Convolutional Neural Networks for Computer-Aided Detection: CNN Architectures, Dataset Characteristics and Transfer Learning", IEEE Transactions on Medical Imaging, vol. 35, No. 5, 2016, pp. 1-14.

International Search Report and Written Opinion received for PCT Application Serial No. PCT/US2018/031754 dated Aug. 16, 2018, 10 pages.

Dimitrievski et al., "High resolution depth reconstruction from monocular images and sparse point clouds using deep convolutional neural network", Proceedings of Spie, vol. 10410, 2017, pp. 1-3.

Hosseini et al., "Derivative Kernels: Numerics and Applications", IEEE Transactions on Image Processing, vol. 26, No. 10, 2017, pp. 1-16.

Aljabar, P., et al., "Multi-atlas based segmentation of brain images: Atlas selection and its effect on accuracy," NeuroImage, vol. 46, No. 3, pp. 726-738 (Jul. 1, 2009).

Curiale, A.H., et al., "Automatic myocardial segmentation by using a deep learning network in cardiac MRI," IEEE XLIII Latin American Computer Conference (CLEI), pp. 1-6 (2017).

International Search Report and Written Opinion issued in connection with corresponding PCT Application No. PCT/US2018/017407 dated Jul. 4, 2018.

Zhang, M., et al., Deep Learning Architecture for Automated Image Feature Extraction, GE Co-Pending U.S. Appl. No. 62/574,333, filed Oct. 19, 2017.

Zhang, M., et al., Training an Auto-Encoder on a Single Class, GE Co-Pending U.S. Appl. No. 15/854,980, filed Dec. 27, 2017.

Zhang, M., et al., Building a Binary Neural Network Architecture, GE Co-Pending U.S. Appl. No. 15/855,015, filed Dec. 27, 2017.

(56) References Cited

OTHER PUBLICATIONS

Non-Final Office Action received for U.S. Appl. No. 15/854,971 dated Sep. 16, 2019, 27 pages.

Notice of Allowance received for U.S. Appl. No. 15/854,980 dated Nov. 15, 2019, 67 pages.

Final Office Action received for U.S. Appl. No. 15/854,971 dated Mar. 18, 2020, 72 pages.

Christ, Patrick Ferdinand, et al., "Automatic liver and tumor segmentation of CT and MRI volumes using cascaded fully convolutional neural networks", arXiv preprint arXiv: 1702.05970, Feb. 23, 2017, 20 pages.

Ravishankar et al., "Joint deep learning of foreground, background and shape for robust contextual segmentation", International Conference on Information Processing in Medical Imaging. Springer, Cham, 2017, pp. 622-632.

Abd-Ellah, Mahmoud Khaled, et al., "TPUAR-Net: Two Parallel U-Net with Asymmetric Residual-Based Deep Convolutional Neural Network for Brain Tumor Segmentation", International Conference on Image Analysis and Recognition. Springer, Cham, 2019, 11 pages.

Notice of Allowance received for U.S. Appl. No. 15/854,971 dated Jun. 8, 2020, 52 pages.

Chen et al. "Towards automatic abdominal multi-organ segmentation in dual energy CT using cascaded 3D fully convolutional network" arXiv preprint arXiv: 1710.05379, 2017, 5 Pages.

Wang et al. "Automatic brain tumor segmentation using cascaded anisotropic convolutional neural networks" International MICCAI brainlesion workshop. Springer, Cham, 2017, 13 pages.

Jegou, Simon, et al. "The one hundred layers tiramisu: Fully convolutional densenets for semantic segmentation." Jegou et al. "The one hundred layers tiramisu: Fully convolutional densenets for semantic segmentation" Proceedings of the IEEE conference on computer vision and pattern recognition workshops, 2017, 09 pages.

Non-Final Office Action received for U.S. Appl. No. 16/573,222 dated Dec. 18, 2020, 105 pages.

Non-Final Office Action received for U.S. Appl. No. 15/855,015 dated Jan. 8, 2021, 64 pages.

Final Office Action received for U.S. Appl. No. 15/855,015 dated Mar. 24, 2021, 33 pages.

Roth et al., "Improving Computer-aided Detection using Convolutional Neural Networks and Random View Aggregation", May 2016, 12 pages.

* cited by examiner

DEVIATION MAP DATA 406

ATLAS MAP DATA 404

MEDICAL IMAGING DATA 402

IMAGE ANALYSIS USING DEVIATION FROM NORMAL DATA

RELATED APPLICATION

This application claims priority to U.S. Provisional Application No. 62/574,333, filed Oct. 19, 2017, and entitled "DEEP LEARNING ARCHITECTURE FOR AUTOMATED IMAGE FEATURE EXTRACTION", the entirety of which is incorporated herein by reference.

TECHNICAL FIELD

This disclosure relates generally to artificial intelligence.

BACKGROUND

Artificial Intelligence (AI) can be employed for classification and/or analysis of digital images. For instance, AI can be employed for image recognition. In certain technical applications, AI can be employed to enhance imaging analysis. In an example, region-of-interest based deep neural networks can be employed to localize a feature in a digital image. However, accuracy and/or efficiency of a classification and/or an analysis of digital images using conventional artificial techniques is generally difficult to achieve. Furthermore, conventional artificial techniques for classification and/or analysis of digital images generally requires labor-intensive processes such as, for example, pixel annotations, voxel level annotations, etc. As such, conventional artificial techniques for classification and/or analysis of digital images can be improved.

SUMMARY

The following presents a simplified summary of the specification in order to provide a basic understanding of some aspects of the specification. This summary is not an extensive overview of the specification. It is intended to neither identify key or critical elements of the specification, nor delineate any scope of the particular implementations of the specification or any scope of the claims. Its sole purpose is to present some concepts of the specification in a simplified form as a prelude to the more detailed description that is presented later.

According to an embodiment, a system includes an atlas map component, a deviation map component, and a neural network component. The atlas map component generates atlas map data indicative of an atlas map that includes a first portion of patient image data from a plurality of reference patients that satisfies a first defined criterion and a second portion of the patient image data from a plurality of target patients that satisfies a second defined criterion. The first portion of the patient image data is matched to a corresponding age group for a set of patient identities associated with the first portion of the patient image data. The second portion of the patient data is associated with a plurality of clinical conditions. The deviation map component generates deviation map data that represents an amount of deviation for the second portion of the patient image data compared to the first portion of the patient image data. The neural network component trains a neural network based on the deviation map data to determine one or more clinical conditions included in image data.

According to another embodiment, a method is provided. The method provides for using a processor operatively coupled to memory to execute computer executable components to perform acts such as generating atlas map data indicative of an atlas map that includes a first portion of patient image data associated with a plurality of reference patients and a second portion of the patient image data associated with a plurality of clinical conditions, where the first portion of the patient image data is matched to a corresponding age group for a set of patient identities associated with the first portion of the patient image data. The method also provides for acts such as generating deviation map data that represents an amount of deviation between the second portion of the patient image data and the first portion of the patient image data. Furthermore, the method provides for acts such as training a neural network based on the deviation map data to determine one or more clinical conditions included in image data.

According to yet another embodiment, a computer readable storage device comprising instructions that, in response to execution, cause a system comprising a processor to perform operations, comprising: generating atlas map data indicative of an atlas map that includes a first portion of patient image data associated with a plurality of reference patients and a second portion of the patient image data associated with a plurality of clinical conditions, where the first portion of the patient image data is matched to a corresponding age group for a set of patient identities associated with the first portion of the patient image data, modifying the atlas map data to generate deviation map data that represents an amount of deviation between the second portion of the patient image data and the first portion of the patient image data, and training a neural network based on the deviation map data to determine one or more clinical conditions included in image data.

The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

Figure 1:
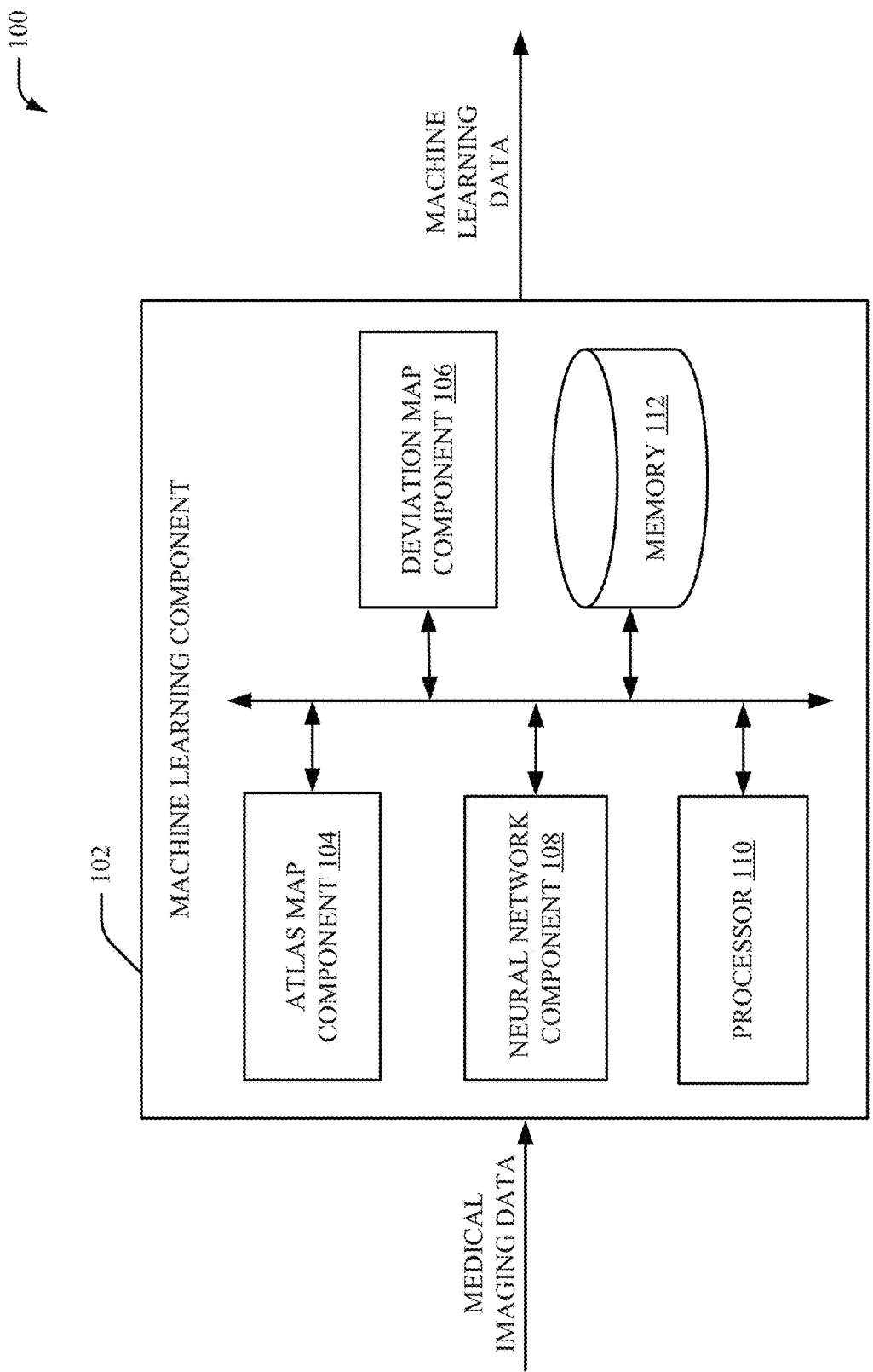
FIG. 1 illustrates a high-level block diagram of an example machine learning component, in accordance with various aspects and implementations described herein.

Various aspects of this disclosure are now described with reference to the drawings, wherein like reference numerals are used to refer to like elements throughout. In the following description, for purposes of explanation, numerous specific details are set forth in order to provide a thorough understanding of one or more aspects. It should be understood, however, that certain aspects of this disclosure may be practiced without these specific details, or with other methods, components, materials, etc. In other instances, well-known structures and devices are shown in block diagram form to facilitate describing one or more aspects.

Systems and techniques for image analysis using deviation from normal data are presented. For example, as compared to conventional artificial intelligence (AI) techniques, the subject innovations provide for a novel AI framework that facilitates image analysis (e.g., brain image analysis) using deviation from normal data. Pediatric brain morphology changes very quickly during the first few years of human life. Furthermore, the changes are known to be highly significant in the first few months of human life and then gradually the rate of change decreases as the human enters adulthood. Because of such rapid changes in morphology of pediatric brains, it is difficult for pediatric neurologists to diagnose age related clinical conditions that manifest differently at different ages. For example, what is normal anatomy in an 18-month-old child may different than pathology in a 4-month-old baby. Therefore, it is beneficial in such cases to conduct age matched pattern matching of various clinical conditions in pediatrics. In an aspect, the novel AI framework disclosed herein can provide a deep learning based classifier that analyses age-matched deviation maps of medical images (e.g., MRI images) to, for example, assist clinicians in diagnosing clinical conditions in pediatric patients.

In an embodiment, age-matched normal patient image data from a plurality of pediatric patients that belong to a plurality of pediatric age groups can be accessed. Normal patient data of a given age group can be registered to an atlas to form a standardized age matched normal patient grouping for the age group. Furthermore, abnormal patient image data for a set of plurality of clinical conditions can be accessed. The abnormal patient image data can be registered to the atlas to form a standardized abnormal patient grouping. A deviation map associated with the abnormal patient image data can be determined in the standardized abnormal patient grouping based on the standardized age-matched normal patient grouping to form a deviation image data collection. Moreover, a neural network can be trained based on the deviation image data collection to determine one or more clinical conditions in patient image data. As such, by employing the novel AI framework as described herein, detection and/or localization of one or more features associated with patient image data (e.g., detection and/or localization of one or more diseases for a patient associated with medical imaging data) can be improved. Furthermore, accuracy and/or efficiency for classification and/or analysis of patient image data (e.g., medical imaging data) can be improved. Moreover, effectiveness of a machine learning model for classification and/or analysis of patient image data (e.g., medical imaging data) can be improved, performance of one or more processors that execute a machine learning model for classification and/or analysis of patient image data (e.g., medical imaging data) can be improved, and/or efficiency of one or more processors that execute a machine learning model for classification and/or analysis of patient image data (e.g., medical imaging data) can be improved.

Referring initially to FIG. 1, there is illustrated an example system 100 for facilitating image analysis using deviation from normal data, according to an aspect of the subject disclosure. The system 100 can be employed by various systems, such as, but not limited to medical device systems, medical imaging systems, medical diagnostic systems, medical systems, medical modeling systems, enterprise imaging solution systems, advanced diagnostic tool systems, simulation systems, image management platform systems, care delivery management systems, artificial intelligence systems, machine learning systems, neural network systems, modeling systems, aviation systems, power systems, distributed power systems, energy management systems, thermal management systems, transportation systems, oil and gas systems, mechanical systems, machine systems, device systems, cloud-based systems, heating systems, HVAC systems, medical systems, automobile systems, aircraft systems, water craft systems, water filtration systems, cooling systems, pump systems, engine systems, prognostics systems, machine design systems, and the like. In one example, the system 100 can be associated with a classification system to facilitate visualization and/or interpretation of medical imaging data. Moreover, the system 100 and/or the components of the system 100 can be employed to use hardware and/or software to solve problems that are highly technical in nature (e.g., related to processing digital data, related to processing medical imaging data, related to medical modeling, related to medical imaging, related to artificial intelligence, etc.), that are not abstract and that cannot be performed as a set of mental acts by a human.

The system 100 can include a machine learning component 102 that can include an atlas map component 104, a deviation map component 106 and a neural network component 108. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. The system 100 (e.g., the machine learning component 102) can include memory 112 for storing computer executable components and instructions. The system 100 (e.g., the machine learning component 102) can further include a processor 110 to facilitate operation of the instructions (e.g., computer executable components and instructions) by the system 100 (e.g., the machine learning component 102).

The machine learning component 102 (e.g., the atlas map component 104) can receive medical imaging data (e.g., MEDICAL IMAGING DATA shown in FIG. 1). The medical imaging data can be two-dimensional medical imaging data and/or three-dimensional medical imaging data generated by one or more medical imaging devices. For example, the medical imaging data can be electromagnetic radiation imagery captured via a set of sensors (e.g., a set of sensors associated with a medical imaging device). In certain embodiments, the medical imaging data can be a series of electromagnetic radiation imagery captured via a set of sensors (e.g., a set of sensors associated with a medical imaging device) during an interval of time. In another example, the medical imaging data can be positron emission tomography (PET) scan imagery. In yet another example, the medical imaging data can be magnetic resonance imaging (MRI) data. The medical imaging data can be received directly from one or more medical imaging devices. Alternatively, the medical imaging data can be stored in one or more databases that receives and/or stores the medical imaging data associated with the one or more medical imaging devices. A medical imaging device can be, for example, an x-ray device, a computed tomography (CT) device, a PET scanner device, an MRI device, another type of medical imaging device, etc. The medical imaging data can also be patient image data associated with one or more patient identities. In a non-limiting embodiment, the medical imaging data can be a set of pediatric brain scan images. Furthermore, at least a portion of the medical imaging data can be matched to a corresponding ag group for a set of patient identities. For example, the medical imaging data can be age-matched patient image data.

The atlas map component 104 can generate atlas map data indicative of an atlas map that includes a first portion of the medical imaging data that satisfies a first defined criterion. In an aspect, the first portion of the medical imaging data can be from a plurality of reference patients. For instance, the first portion of the medical imaging data can be reference data from a plurality of patients. Furthermore, the first portion of the medical imaging data can be matched to a corresponding age group for a set of patient identities associated with the first portion of the medical imaging data. For example, the first portion of the medical imaging data can be age-matched normal medical imaging data from a plurality of pediatric patients that belong to a plurality of pediatric age groups. Additionally, the atlas map data generated by the atlas map component 104 can include a second portion of the medical imaging data that satisfies a second defined criterion. For example, the second portion of the medical imaging data can be abnormal medical imaging data associated with one or more abnormal medical conditions. In an aspect, the second portion of the medical imaging data can be from a plurality of target patients. Additionally, the second portion of the medical imaging data can be associated with a plurality of clinical conditions. For instance, the first portion of the medical imaging data can be target data from a plurality of patients for each of a plurality of clinical conditions (e.g., for each of a plurality of disease conditions).

In an aspect, the atlas map component 104 can group the first portion of the medical imaging data in the atlas map data based on a set of age groups for the set of patient identities. For example, the atlas map component 104 can form one or more age-matched normal medical imaging data groups within the atlas map data. In another aspect, the atlas map component 104 can configure a first portion of the atlas map data as a set of age-matched groupings associated with the first portion of the medical imaging data. Furthermore, the atlas map component 104 can configure a second portion of the atlas map data as a set of abnormal medical condition groupings associated with the second portion of the medical imaging data. In yet another aspect, the atlas map component 104 can format the atlas map data as a matrix of numerical data values that represent the first portion of the medical imaging data and the second portion of the medical imaging data. For example, the atlas map data can represent a set of z-scores (e.g., a set of standard deviation scores) for the first portion of the medical imaging data and the second portion of the medical imaging data. In certain embodiments, the atlas map component 104 can normalize the first portion of medical imaging data and/or the second portion of medical imaging data to generate the atlas map data. For example, the atlas map component 104 can employ one or more normalization techniques to normalize numerical data values that represent the first portion of the medical imaging data and the second portion of the medical imaging data. In a non-limiting example, the atlas map component 104 can employ a feature scaling technique to normalize numerical data values that represent the first portion of the medical imaging data and the second portion of the medical imaging data. In an embodiment, atlas map data can represent a statistical representation of the first portion of the medical imaging data and/or the second portion of the medical imaging data. For example, for each data value of the atlas map data, the atlas map component 104 can generate an image intensity value associated with a mean value and a standard deviation value. In an aspect, the atlas map component 104 can generate a statistical representation of reference data by, for example, point-by-point intensity value mean and intensity value standard deviation from all patient data in the reference data. The statistical representation can be associated with a mean value and a standard deviation value at each image intensity value within the atlas map data.

The deviation map component 106 can generate deviation map data that represents an amount of deviation for the second portion of the medical imaging data compared to the first portion of medical imaging data. In an aspect, the deviation map component 106 can modify the atlas map data to generate deviation map data. For example, the deviation map component 106 can alter one or more visual characteristics of numerical data values included in the atlas map data. In one example, the deviation map component 106 can alter one or more visual characteristics of the matrix of numerical data values in the atlas data to generate the deviation map data. In another example, the deviation map component can convert the matrix of numerical data values into a matrix of colorized data values formatted based on the amount of deviation for the second portion of the medical imaging data compared to the first portion of medical imaging data. In certain embodiments, the deviation map data can include a set of colors that correspond to different numerical values for the atlas map data. For example, a first color (e.g., a color blue) in the deviation map data can correspond to a first value (e.g., a normal medical condition) for the atlas map data, a second color (e.g., a color green) in the deviation map data can correspond to a second value (e.g., a possible abnormal medical condition) for the atlas map data, a third color (e.g., a color red) in the deviation map data can correspond to a third value (e.g., an abnormal medical condition) for the atlas map data, etc. In an embodiment, the deviation map component 106 can subtract the mean value from the image intensity value associated with each data value of the atlas map data to generate a difference value. Furthermore, the deviation map component 106 can divide the difference value by the standard deviation value to facilitate generation of the deviation map data. In certain embodiments, a deviation map can be generated for each target image by subtracting a mean value from an intensity value and dividing a difference between the mean value and the intensity value by a standard deviation of intensity values associated with a corresponding location within an atlas map. As such, a set of deviation maps corresponding to each image for each of a plurality of clinical conditions can be generated.

The neural network component 108 can train a neural network based on the deviation map data to determine one or more clinical conditions included in medical imaging data. For example, the deviation map data can be provided as input to a neural network. Furthermore, the neural network can perform a machine learning training process (e.g., an artificial intelligence training process for machine learning) based on the deviation map data. As such, the deviation map data can be employed to train a neural network to classify one or more clinical conditions based on a set of deviations maps rather than original medical imaging data. In an embodiment, dimensionality of the neural network can be two-dimensional. In another embodiment, dimensionality of the neural network can be three-dimensional. In an aspect, the neural network component 108 can train the neural network based on the deviation map data to generate a trained neural network. The neural network can be, for example, a spring network of convolutional layers. For instance, the neural network can perform a plurality of sequential and/or parallel downsampling and upsampling of the deviation map data associated with convolutional layers of the neural network. In an example, the neural network component 108 can perform a first convolutional layer process associated with sequential downsampling of the deviation map data and a second convolutional layer process associated with sequential upsampling of the deviation map data. The spring network of convolutional layers can include the first convolutional layer process associated with the sequential downsampling and the second convolutional layer process associated with sequential upsampling. The spring network of convolutional layers employed by the neural network component 108 can alter convolutional layer filters similar to functionality of a spring. For instance, the neural network component 108 can analyze the deviation map data based on a first convolutional layer filter that comprises a first size, a second convolutional layer filter that comprises a second size that is different than the first size, and a third convolutional layer filter that comprises the first size associated with the first convolutional layer filter.

In an embodiment, the neural network component 108 can generate machine learning data (e.g., MACHINE LEARNING DATA shown in FIG. 1). The machine learning data can include, for example, a set of filter values for the neural network based on the training phase associated with the deviation map data. In another example, the machine learning data can include a set of as set of weights for a set of filters associated with the neural network (e.g., the neural network model) based on the training phase associated with the deviation map data. In certain embodiments, the machine learning data can include information that is indicative of correlations, inferences and/or expressions associated with the deviation map data.

It is to be appreciated that technical features of the machine learning component 102 are highly technical in nature and not abstract ideas. Processing threads of the machine learning component 102 that process and/or analyze the medical imaging data, determine outlier medical imaging data, etc. cannot be performed by a human (e.g., are greater than the capability of a single human mind). For example, the amount of the medical imaging data processed, the speed of processing of the medical imaging data and/or the data types of the medical imaging data processed by the machine learning component 102 over a certain period of time can be respectively greater, faster and different than the amount, speed and data type that can be processed by a single human mind over the same period of time. Furthermore, the medical imaging data processed by the machine learning component 102 can be one or more medical images generated by sensors of a medical imaging device. Moreover, the machine learning component 102 can be fully operational towards performing one or more other functions (e.g., fully powered on, fully executed, etc.) while also processing the medical imaging data.

Figure 2:
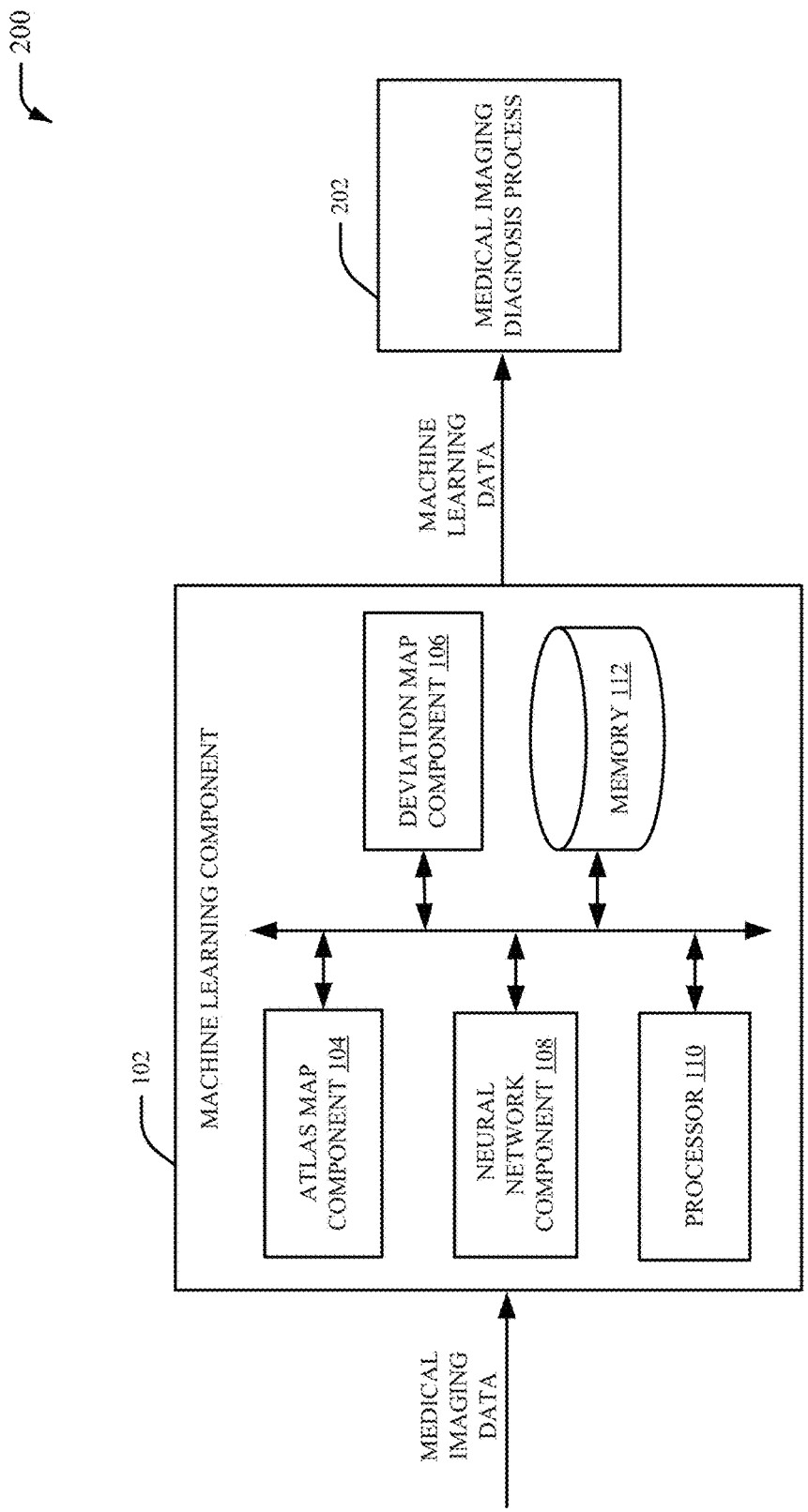
FIG. 2 illustrates a system that includes an example machine learning component and an example medical imaging diagnosis process, in accordance with various aspects and implementations described herein.

Referring now to FIG. 2, there is illustrated a non-limiting implementation of a system 200 in accordance with various aspects and implementations of this disclosure. Repetitive description of like elements employed in other embodiments described herein is omitted for sake of brevity.

The system 200 includes the machine learning component 102 and a medical imaging diagnosis process 202. The machine learning component 102 can include the atlas map component 104, the deviation map component 106, the neural network component 108, the processor 110 and/or the memory 112. The machine learning component 102 can provide, for example, the machine learning data to the medical imaging diagnosis process 202. In an aspect, the medical imaging diagnosis process 202 can perform deep learning to facilitate classification and/or localization of one or more diseases associated with medical imaging data. In another aspect, the medical imaging diagnosis process 202 can perform deep learning based on a convolutional neural network that receives medical imaging data. A disease classified and/or localized by the medical imaging diagnosis process 202 can include, for example, a lung disease, a heart disease, a tissue disease, a bone disease, a tumor, a cancer, tuberculosis, cardiomegaly, hypoinflation of a lung, opacity of a lung, hyperdistension, a spine degenerative disease, calcinosis, or another type of disease associated with an anatomical region of a patient body. In an aspect, the medical imaging diagnosis process 202 can determine a prediction for a disease associated with medical imaging data. For example, the medical imaging diagnosis process 202 can determine a probability score for a disease associated with medical imaging data (e.g., a first percentage value representing likelihood of a negative prognosis for the disease and a second value representing a likelihood of a positive prognosis for the disease).

Figure 3:
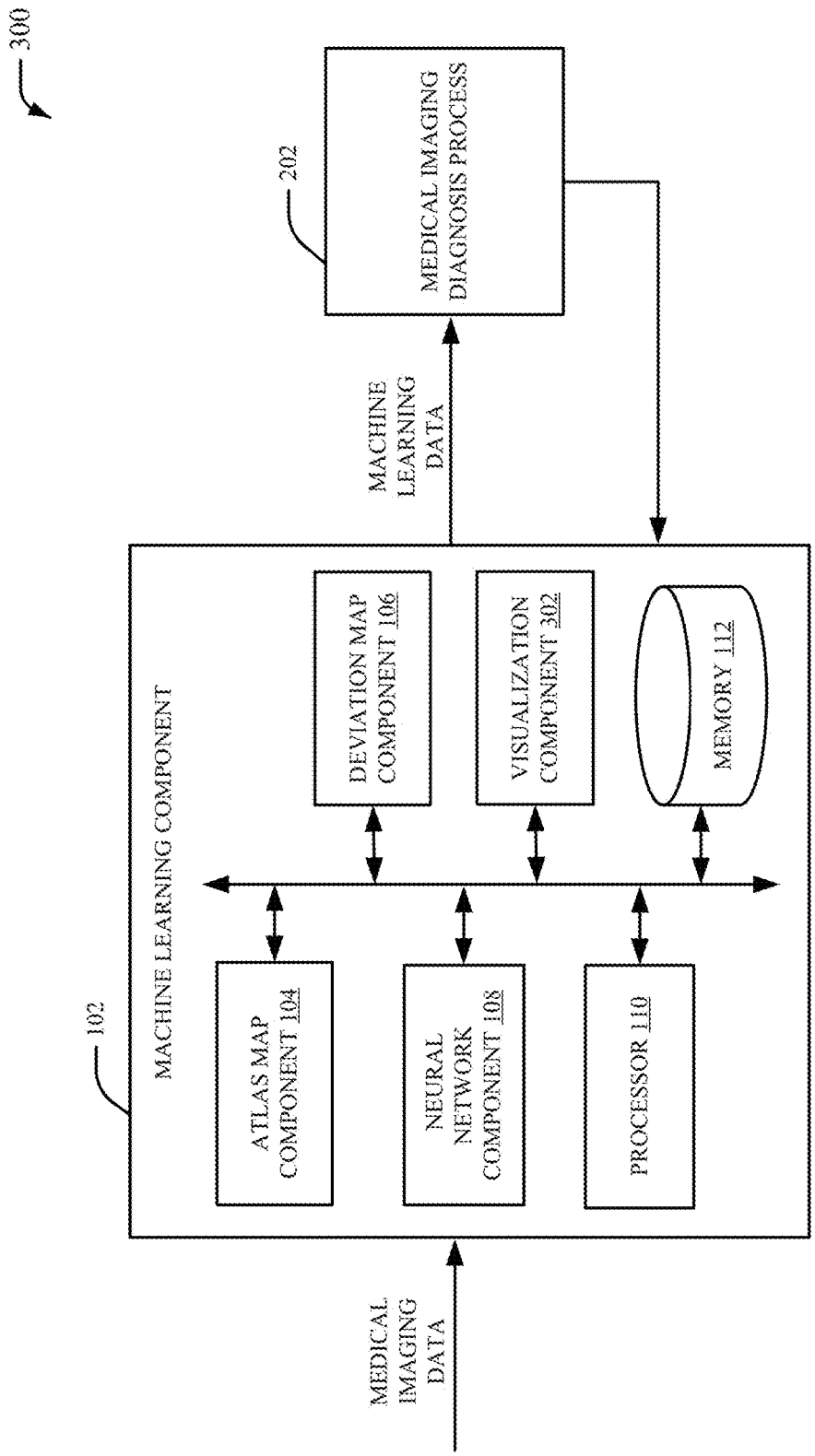
FIG. 3 illustrates a high-level block diagram of another example machine learning component, in accordance with various aspects and implementations described herein.

Referring now to FIG. 3, there is illustrated a non-limiting implementation of a system 300 in accordance with various aspects and implementations of this disclosure. Repetitive description of like elements employed in other embodiments described herein is omitted for sake of brevity.

The system 300 includes the machine learning component 102. The machine learning component 102 can include the atlas map component 104, the deviation map component 106, the neural network component 108, the processor 110, the memory 112, and/or a visualization component 302. In an embodiment, the system 300 can further include the medical imaging diagnosis process 202. The visualization component 302 can generate a human-interpretable visualization of one or more clinical conditions included in medical image data. For example, the visualization component 302 can generate a human-interpretable visualization of medical imaging diagnosis data determined by the medical imaging diagnosis process 202. In an embodiment, the visualization component 302 can generate a multi-dimensional visualization associated with classification of one or more clinical conditions included in medical image data. In another embodiment, the visualization component 302 can generate deep learning data based on a classification and/or a localization for a portion of an anatomical region associated with one or more clinical conditions included in medical image data. The deep learning data can include, for example, a classification and/or a location for one or more diseases located in medical imaging data. In certain embodiments, the deep learning data can include probability data indicative of a probability for one or more diseases being located in medical imaging data. The probability data can be, for example, a probability array of data values for one or more diseases being located in medical imaging data. Additionally or alternatively, the visualization component 302 can generate a multi-dimensional visualization associated with classification and/or localization for a portion of an anatomical region associated with medical imaging data.

The multi-dimensional visualization can be a graphical representation of medical imaging data that shows a classification and/or a location of one or more diseases with respect to a patient body. The visualization component 302 can also generate a display of the multi-dimensional visualization of the diagnosis provided by the medical imaging diagnosis process 202. For example, the visualization component 302 can render a 2D visualization of a portion of an anatomical region on a user interface associated with a display of a user device such as, but not limited to, a computing device, a computer, a desktop computer, a laptop computer, a monitor device, a smart device, a smart phone, a mobile device, a handheld device, a tablet, a portable computing device or another type of user device associated with a display. In an aspect, the multi-dimensional visualization can include deep learning data. In another aspect, the deep learning data can also be rendered on the 3D model as one or more dynamic visual elements. The visualization component 302 can, in an embodiment, alter visual characteristics (e.g., color, size, hues, shading, etc.) of at least a portion of the deep learning data associated with the multi-dimensional visualization based on the classification and/or the localization for the portion of the anatomical region. For example, the classification and/or the localization for the portion of the anatomical region can be presented as different visual characteristics (e.g., colors, sizes, hues or shades, etc.), based on a result of deep learning and/or medical imaging diagnosis by the medical imaging diagnosis process 202. In another aspect, the visualization component 302 can allow a user to zoom into or out with respect to the deep learning data associated with the multi-dimensional visualization. For example, the visualization component 302 can allow a user to zoom into or out with respect to a classification and/or a location of one or more diseases identified in the anatomical region of the patient body. As such, a user can view, analyze and/or interact with the deep learning data associated with the multi-dimensional visualization for medical imaging data (e.g., for one or more clinical conditions included in medical image data).

Figure 4:
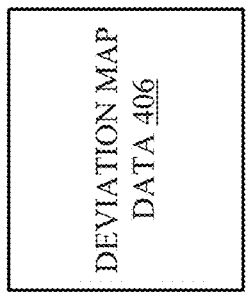
FIG. 4 illustrates an example system associated with medical imaging data, atlas map data, and deviation map data, in accordance with various aspects and implementations described herein.
Figure 4:
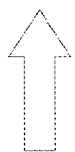
Figure 4:
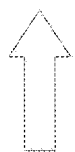

Referring now to FIG. 4, there is illustrated a non-limiting implementation of a system 400 in accordance with various aspects and implementations of this disclosure. Repetitive description of like elements employed in other embodiments described herein is omitted for sake of brevity.

The system 400 includes medical imaging data 402, atlas map data 404 and deviation map data 406. The medical imaging data 402 can correspond to, for example, the medical imaging data received by the machine learning component 102 (e.g., the atlas map component 104). In an embodiment, the medical imaging data 402 can be two-dimensional medical imaging data and/or three-dimensional medical imaging data generated by one or more medical imaging devices. For example, the medical imaging data 402 can be electromagnetic radiation imagery captured via a set of sensors (e.g., a set of sensors associated with a medical imaging device). In certain embodiments, the medical imaging data 402 can be a series of electromagnetic radiation imagery captured via a set of sensors (e.g., a set of sensors associated with a medical imaging device) during an interval of time. In another example, the medical imaging data 402 can be PET scan imagery. In yet another example, the medical imaging data 402 can be MRI data. The medical imaging data 402 can be received directly from one or more medical imaging devices. Alternatively, the medical imaging data 402 can be stored in one or more databases that receives and/or stores the medical imaging data associated with the one or more medical imaging devices. A medical imaging device can be, for example, an x-ray device, a CT device, a PET scanner device, an MRI device, another type of medical imaging device, etc. The medical imaging data 402 can also be patient image data associated with one or more patient identities. In certain embodiments, the medical imaging data 402 can be a set of pediatric brain scan images. Furthermore, at least a portion of the medical imaging data 402 can be matched to a corresponding ag group for a set of patient identities. For example, the medical imaging data 402 can be age-matched patient image data.

The machine learning component 102 (e.g., the atlas map component 104) can generate the atlas map data 404 based on the medical imaging data 402. The atlas map data 404 can be indicative of an atlas map that includes a first portion of the medical imaging data 402 that satisfies a first defined criterion and a second portion of the medical imaging data 402 that satisfies a second defined criterion. The first portion of the medical imaging data 402 can be matched to a corresponding age group for a set of patient identities associated with the first portion of the medical imaging data 402. For example, the first portion of the medical imaging data 402 can be age-matched normal medical imaging data from a plurality of pediatric patients that belong to a plurality of pediatric age groups. The second portion of the medical imaging data 402 can be abnormal medical imaging data associated with one or more abnormal medical conditions. In an aspect, the first portion of the medical imaging data 402 can be formatted in the atlas map data 404 based on a set of age groups for the set of patient identities. For example, the atlas map data 404 can include one or more age-matched normal medical imaging data groups. In another aspect, a first portion of the atlas map data 404 can be configured as a set of age-matched groupings associated with the first portion of the medical imaging data 402. Furthermore, a second portion of the atlas map data 404 can be configured as a set of abnormal medical condition groupings associated with the second portion of the medical imaging data 402. In yet another aspect, atlas map data 404 can be a matrix of numerical data values that represent the first portion of the medical imaging data 402 and the second portion of the medical imaging data 402. For example, the atlas map data 404 can represent a set of z-scores (e.g., a set of standard deviation scores) for the first portion of the medical imaging data 402 and the second portion of the medical imaging data 402.

The machine learning component 102 (e.g., the deviation map component 106) can alter the atlas map data 404 to generate the deviation map data 406. The deviation map data 406 can represent an amount of deviation between the second portion of the medical imaging data 402 and the first portion of medical imaging data 402. In an aspect, different visual characteristics of the deviation map data 406 can be configured to represent different values included in the atlas map data 404. In one example, a matrix of numerical data values included in the atlas map data 404 can be converted into a matrix of colorized data values in the deviation map data 406. The matrix of colorized data values in the deviation map data 406 can be formatted based on the amount of deviation between the second portion of the medical imaging data 402 and the first portion of medical imaging data 402. In certain embodiments, the deviation map data 406 can include a set of colors that correspond to different numerical values for the atlas map data 404. For example, a first color (e.g., a color blue) in the deviation map data 406 can correspond to a first value (e.g., a normal medical condition) for the atlas map data 404, a second color (e.g., a color green) in the deviation map data 406 can correspond to a second value (e.g., a possible abnormal medical condition) for the atlas map data 404, a third color (e.g., a color red) in the deviation map data 406 can correspond to a third value (e.g., an abnormal medical condition) for the atlas map data 404, etc.

Figure 5:
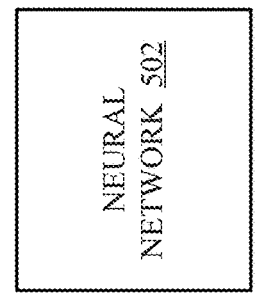
FIG. 5 illustrates an example system associated with deviation map data and a neural network, in accordance with various aspects and implementations described herein.
Figure 5:
Figure 5:
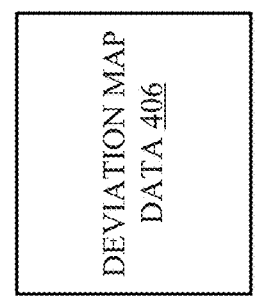

Referring now to FIG. 5, there is illustrated a non-limiting implementation of a system 500 in accordance with various aspects and implementations of this disclosure. Repetitive description of like elements employed in other embodiments described herein is omitted for sake of brevity.

The system 500 includes the deviation map data 406 and a neural network 502. In an embodiment, the neural network 502 can be trained based on the deviation map data 406. For example, a machine learning training phase can be performed for the neural network 502 based on the deviation map data 406 to train the neural network 502. The neural network 502 can be trained based on the deviation map data 406 to, for example, determine one or more clinical conditions included in medical imaging data. In an aspect, a set of filter values for the neural network 502 can be determined based on the deviation map data 406. In another aspect, a set of weights for a set of filters associated with the neural network 502 can be determined based on the deviation map data 406. The neural network 502 can be, for example, a spring network of convolutional layers. For instance, the neural network 502 by performing sequential and/or parallel downsampling and upsampling of the deviation map data associated with convolutional layers of the neural network 502. In an example, the neural network 502 can perform a first convolutional layer process associated with sequential downsampling of the deviation map data 406 and a second convolutional layer process associated with sequential upsampling of the deviation map data 406. The spring network of convolutional layers associated with the neural network 502 can include the first convolutional layer process associated with the sequential downsampling and the second convolutional layer process associated with sequential upsampling. The spring network of convolutional layers associated with the neural network 502 can alter convolutional layer filters similar to functionality of a spring. For instance, the neural network 502 can analyze the deviation map data 406 based on a first convolutional layer filter that comprises a first size, a second convolutional layer filter that comprises a second size that is different than the first size, and a third convolutional layer filter that comprises the first size associated with the first convolutional layer filter. In an embodiment, dimensionality of the neural network 502 can be two-dimensional. In another embodiment, dimensionality of the neural network 502 can be three-dimensional.

Figure 6:
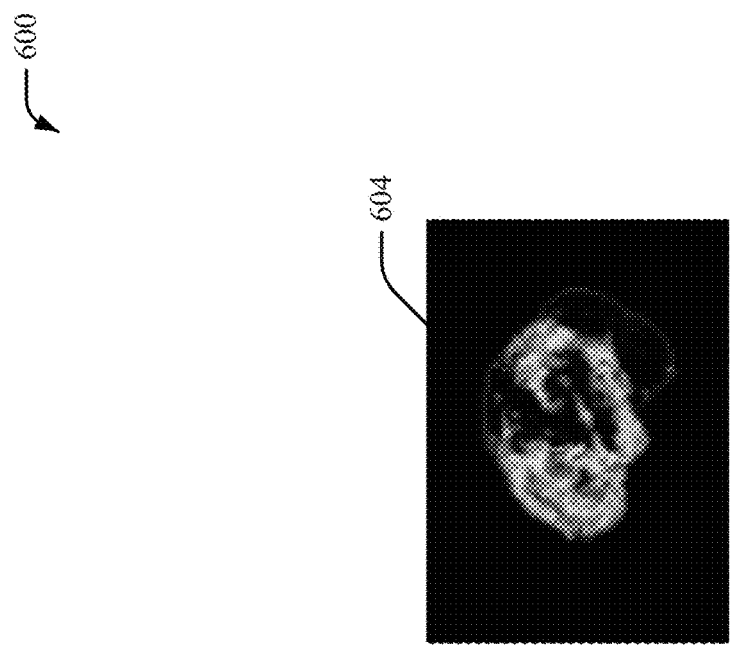
FIG. 6 illustrates an example system associated with deviation map data and multi-dimensional visualization data, in accordance with various aspects and implementations described herein.
Figure 6:
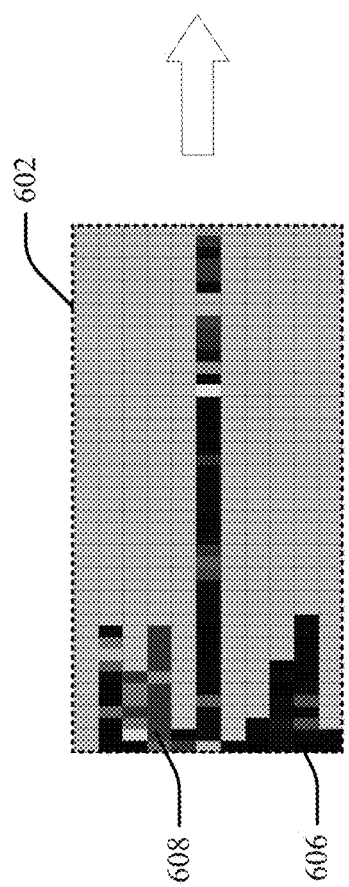

Referring now to FIG. 6, there is illustrated a non-limiting implementation of a system 600 in accordance with various aspects and implementations of this disclosure. Repetitive description of like elements employed in other embodiments described herein is omitted for sake of brevity.

The system 600 includes deviation map data 602 and multi-dimensional visualization data 604. In an embodiment, the deviation map data 602 can correspond to the deviation map data 406. The deviation map data 602 can include different visual characteristics that represent different values included in atlas map data. For instance, the deviation map data 602 can include a set of colors that correspond to different numerical values for atlas map data. In an aspect, the deviation map data 602 can be a matrix of colorized data values. For example, the deviation map data 406 can include at least a first colorized data value 606 and a second colorized data value 608. The first colorized data value 606 can be, for example, formatted as a blue color to represent a normal medical condition in medical imaging data. The second colorized data value 608 can be, for example, formatted as a red color to represent an abnormal medical condition in medical imaging data. In an embodiment, the deviation map data 602 can be employed to train a neural network (e.g., neural network 502) and/or to determine one or more clinical conditions included in medical imaging data. The multi-dimensional visualization data 604 can display one or more predicted locations for a disease associated with medical imaging data. Visual characteristics (e.g., a color, a size, hues, shading, etc.) of the multi-dimensional visualization data 604 can be dynamic based on information provided by the deviation map data 602. For instance, a first portion of the multi-dimensional visualization data 604 can comprise a first visual characteristic, a second portion of the multi-dimensional visualization data 604 can comprise a second visual characteristic, a third portion of the multi-dimensional visualization data 604 can comprise a third visual characteristic, etc. In an aspect, different visual characteristics of the multi-dimensional visualization data 604 can represent different degrees of likelihood for a disease associated with medical imaging data.

Figure 7:
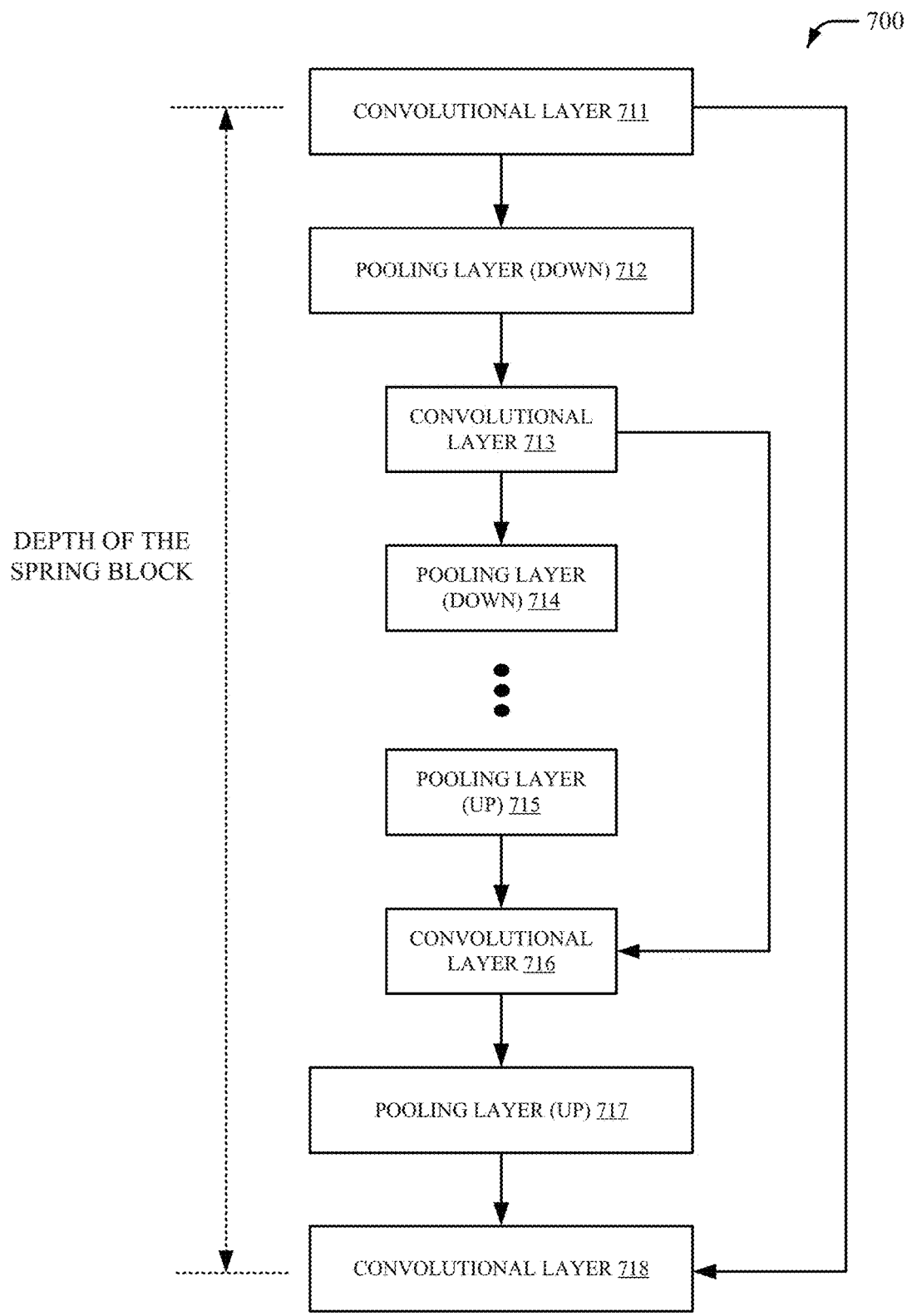
FIG. 7 illustrates a high-level block diagram of an example spring block associated with a neural network, in accordance with various aspects and implementations described herein.

Referring now to FIG. 7, there is illustrated a non-limiting implementation of a system 700 in accordance with various aspects and implementations of this disclosure. The system 700 can illustrate an example spring block for a deep learning architecture associated with a neural network. For example, the system 700 can correspond to a neural network (e.g., neural network 502) employed by the neural network component 108. The spring block associated with the system 700 can be associated with sequential upsampling and downsampling for a spring deep learning network. In an aspect, the spring block associated with the system 700 can consist of connected pair down sampling/up sampling layers and convolutional layers. The spring block associated with the system 700 can also be very flexible in terms of depth (e.g., number of paired up/down sampling convolutional layers) and/or size of convolutional filters (e.g. a convolutional filter size equal to 3×3, a convolutional filter size equal to 5×5, a convolutional filter size equal to 7×7, etc.).

In an embodiment, the system 700 can include a convolutional layer 711. The convolutional layer 711 can be a first convolutional layer of a neural network (e.g., neural network 502) that processes deviation map data. Furthermore, the convolutional layer 711 can be associated with a first filter size. The convolutional layer 711 can be followed by a pooling layer (down) 712. The pooling layer (down) 712 can be associated with downsampling. For instance, the pooling layer (down) 712 can reduce dimensionality of data generated by the convolutional layer 711. In one example, the pooling layer (down) 712 can reduce dimensionality of a feature map for deviation map data processed by the convolutional layer 711. The pooling layer (down) 712 can be followed by a convolutional layer 713. The convolutional layer 713 can be a second convolutional layer of the neural network (e.g., neural network 502) that processes deviation map data. Furthermore, the convolutional layer 713 can be associated with a second filter size that is different than the first filter size associated with the convolutional layer 711. For example, the second filter size associated with the convolutional layer 713 can be smaller than the first filter size associated with the convolutional layer 711. The convolutional layer 713 can be followed by a pooling layer (down) 714. The pooling layer (down) 714 can be associated with downsampling. For instance, the pooling layer (down) 714 can reduce dimensionality of data generated by the convolutional layer 713. In one example, the pooling layer (down) 714 can reduce dimensionality of a feature map for deviation map data processed by the convolutional layer 713. The pooling layer (down) 714 can be followed by a convolutional layer (not shown), which, in turn, can be followed by a pooling layer (up) 715. However, in certain embodiments, the pooling layer (down) 714 can be followed by one or more other convolutional layers and/or one or more other pooling layers (down) prior to the pooling layer (up) 715 to further process deviation map data with different filter sizes and/or further reduction to dimensionality of data. The pooling layer (up) 715 can be associated with upsampling. For instance, the pooling layer (up) 715 can increase dimensionality of data generated by one or more convolutional layers. In one example, the pooling layer (up) 715 can increase dimensionality of a feature map for deviation map data processed by one or more convolutional layers. The pooling layer (up) 715 can be followed by a convolutional layer 716. The convolutional layer 716 can be, for example, a third convolutional layer of the neural network (e.g., neural network 502) that processes the deviation map data. Furthermore, the convolutional layer 716 can be associated with the second filter size associated with the convolutional layer 713.

The convolutional layer 716 can be followed by a pooling layer (up) 717. The pooling layer (up) 717 can be associated with upsampling. For instance, the pooling layer (up) 717 can increase dimensionality of data generated by the convolutional layer 716. In one example, the pooling layer (up) 717 can increase dimensionality of a feature map for deviation map data processed by the convolutional layer 716. The pooling layer (up) 717 can be followed by a convolutional layer 718. The convolutional layer 718 can be, for example, a fourth convolutional layer of the neural network (e.g., neural network 502) that processes the deviation map data. Furthermore, the convolutional layer 718 can be associated with the first filter size associated with the convolutional layer 716. As such, the spring block associated with the system 700 can behave similar to functionality of a spring where a filter size for one or more convolutional layers are repeated while processing deviation map data via a neural network (e.g., neural network 502).

Figure 8:
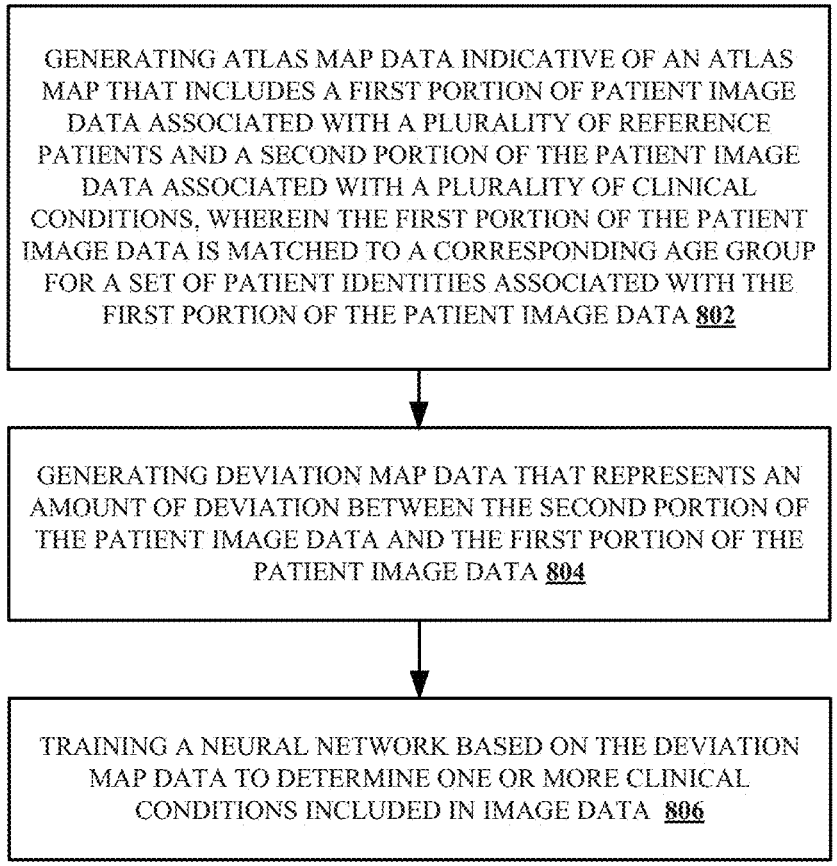
FIG. 8 depicts a flow diagram of an example method for image analysis using deviation from normal data, in accordance with various aspects and implementations described herein.

FIG. 8 illustrates a methodology and/or a flow diagram in accordance with the disclosed subject matter. For simplicity of explanation, the methodology is depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodology in accordance with the disclosed subject matter. In addition, those skilled in the art will understand and appreciate that the methodology could alternatively be represented as a series of interrelated states via a state diagram or events. Additionally, it should be further appreciated that methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device or storage media.

Referring to FIG. 8, there is illustrated a non-limiting implementation of a methodology 800 for facilitating image analysis using deviation from normal data, according to an aspect of the subject innovation. At 802, atlas map data is generated (e.g., by atlas map component 104). The atlas map data is indicative of an atlas map that includes a first portion of patient image data associated with a plurality of reference patients and a second portion of the patient image data associated with a plurality of clinical conditions. The first portion of the patient image data is matched to a corresponding age group for a set of patient identities associated with the first portion of the patient image data. In one example, the patient image data can be medical imaging data. In an embodiment, the patient image data can be two-dimensional patient image data and/or three-dimensional patient image data generated by one or more medical imaging devices. For example, the patient image data can be electromagnetic radiation imagery captured via a set of sensors (e.g., a set of sensors associated with a medical imaging device). In certain embodiments, the patient image data can be a series of electromagnetic radiation imagery captured via a set of sensors (e.g., a set of sensors associated with a medical imaging device) during an interval of time. In another example, the patient image data can be PET scan imagery. In yet another example, the patient image data can be MRI data. The patient image data can be received directly from one or more medical imaging devices. Alternatively, the patient image data can be stored in one or more databases that receives and/or stores the medical imaging data associated with the one or more medical imaging devices. A medical imaging device can be, for example, an x-ray device, a CT device, a PET scanner device, an MRI device, another type of medical imaging device, etc. The patient image data can also be patient image data associated with one or more patient identities. In certain embodiments, the patient image data can be a set of pediatric brain scan images. Furthermore, at least a portion of the patient image data can be matched to a corresponding ag group for a set of patient identities. For example, the patient image data can be age-matched patient image data.

The atlas map data can be indicative of an atlas map that includes a first portion of the patient image data that satisfies a first defined criterion and a second portion of the patient image data that satisfies a second defined criterion. The first portion of the patient image data can be matched to a corresponding age group for a set of patient identities associated with the first portion of the patient image data. For example, the first portion of the patient image data can be age-matched normal medical imaging data from a plurality of pediatric patients that belong to a plurality of pediatric age groups. The second portion of the patient image data can be abnormal medical imaging data associated with one or more abnormal medical conditions. In an aspect, the first portion of the patient image data can be formatted in the atlas map data based on a set of age groups for the set of patient identities. For example, the atlas map data can include one or more age-matched normal medical imaging data groups. In another aspect, a first portion of the atlas map data can be configured as a set of age-matched groupings associated with the first portion of the patient image data. Furthermore, a second portion of the atlas map data can be configured as a set of abnormal medical condition groupings associated with the second portion of the patient image data. In yet another aspect, atlas map data can be a matrix of numerical data values that represent the first portion of the patient image data and the second portion of the patient image data. For example, the atlas map data can represent a set of z-scores (e.g., a set of standard deviation scores) for the first portion of the patient image data and the second portion of the patient image data. In certain embodiments, the atlas map data can be generated by normalizing the first portion of the patient image data and the second portion of the patient image data.

At 804, deviation map data is generated (e.g., by deviation map component 106) that represents an amount of deviation between the second portion of the patient image data and the first portion of the patient image data. In an aspect, different visual characteristics of the deviation map data can be configured to represent different values included in the atlas map data. In one example, a matrix of numerical data values included in the atlas map data can be converted into a matrix of colorized data values in the deviation map data. The matrix of colorized data values in the deviation map data can be formatted based on the amount of deviation between the second portion of the patient image data and the first portion of the patient image data. In certain embodiments, the deviation map data can include a set of colors that correspond to different numerical values for the atlas map data. For example, a first color (e.g., a color blue) in the deviation map data can correspond to a first value (e.g., a normal medical condition) for the atlas map data, a second color (e.g., a color green) in the deviation map data can correspond to a second value (e.g., a possible abnormal medical condition) for the atlas map data, a third color (e.g., a color red) in the deviation map data can correspond to a third value (e.g., an abnormal medical condition) for the atlas map data, etc.

At 806, a neural network is trained (e.g., by neural network component 108) based on the deviation map data to determine one or more clinical conditions. For example, a machine learning training phase can be performed for the neural network based on the deviation map data to train the neural network. The neural network can be trained based on the deviation map data to, for example, determine one or more clinical conditions included in patient image data. In an aspect, a set of filter values for the neural network can be determined based on the deviation map data. In another aspect, a set of weights for a set of filters associated with the neural network can be determined based on the deviation map data. The neural network can be, for example, a spring network of convolutional layers. For instance, the neural network by performing sequential and/or parallel downsampling and upsampling of the deviation map data associated with convolutional layers of the neural network. In an example, the neural network can perform a first convolutional layer process associated with sequential downsampling of the deviation map data and a second convolutional layer process associated with sequential upsampling of the deviation map data. The spring network of convolutional layers associated with the neural network can include the first convolutional layer process associated with the sequential downsampling and the second convolutional layer process associated with sequential upsampling. The spring network of convolutional layers associated with the neural network can alter convolutional layer filters similar to functionality of a spring. For instance, the neural network can analyze the deviation map data based on a first convolutional layer filter that comprises a first size, a second convolutional layer filter that comprises a second size that is different than the first size, and a third convolutional layer filter that comprises the first size associated with the first convolutional layer filter.

The aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

Figure 9:
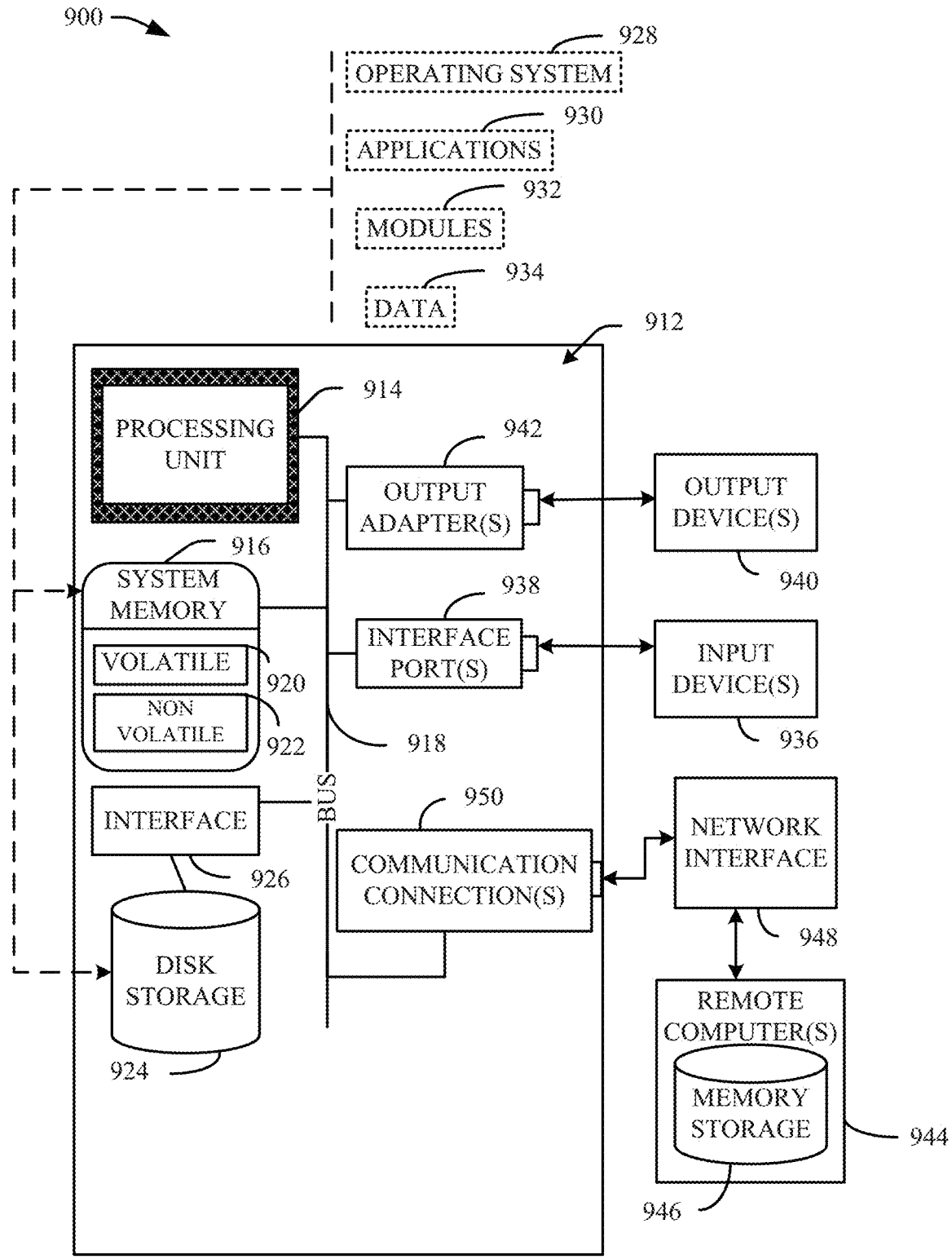
FIG. 9 is a schematic block diagram illustrating a suitable operating environment.
Figure 10:
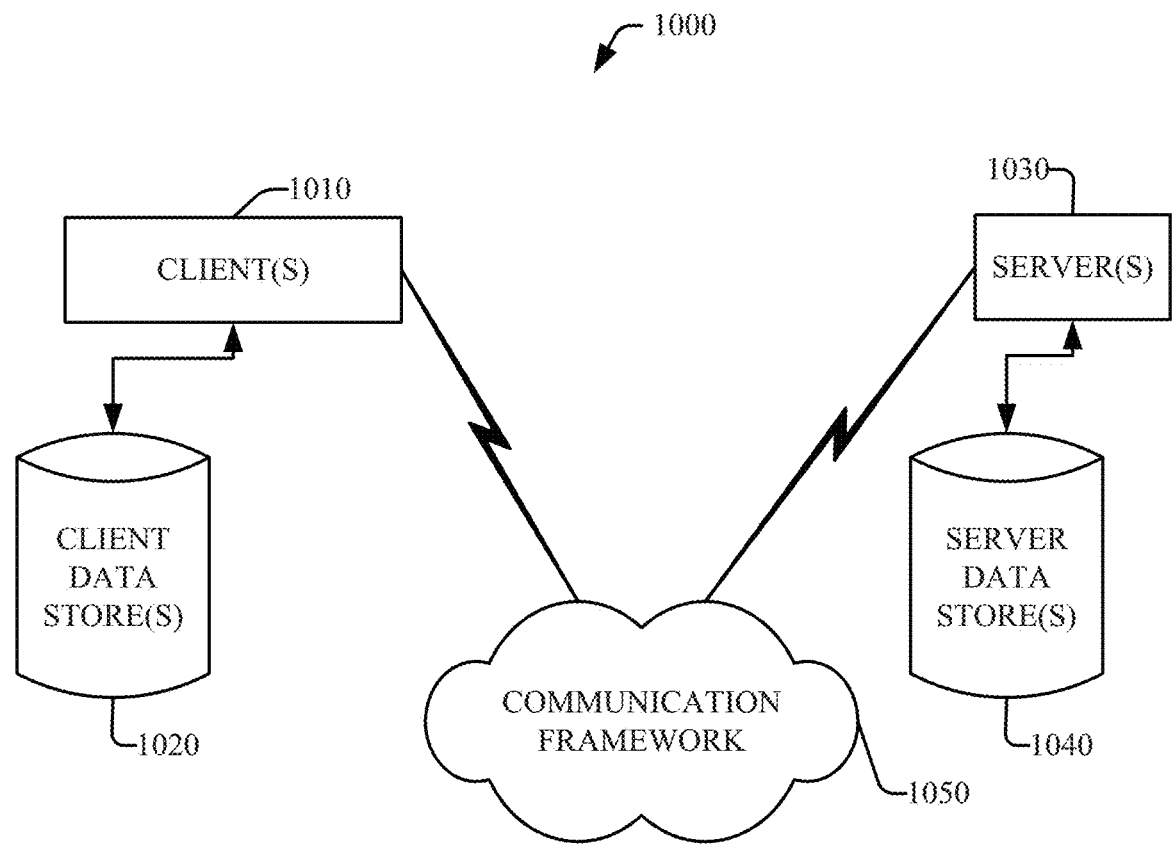
FIG. 10 is a schematic block diagram of a sample-computing environment.

In order to provide a context for the various aspects of the disclosed subject matter, FIGS. 9 and 10 as well as the following discussion are intended to provide a brief, general description of a suitable environment in which the various aspects of the disclosed subject matter may be implemented.

With reference to FIG. 9, a suitable environment 900 for implementing various aspects of this disclosure includes a computer 912. The computer 912 includes a processing unit 914, a system memory 916, and a system bus 918. The system bus 918 couples system components including, but not limited to, the system memory 916 to the processing unit 914. The processing unit 914 can be any of various available processors. Dual microprocessors and other multiprocessor architectures also can be employed as the processing unit 914.

The system bus 918 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 916 includes volatile memory 920 and nonvolatile memory 922. The basic input/output system (BIOS), containing the basic routines to transfer information between elements within the computer 912, such as during start-up, is stored in nonvolatile memory 922. By way of illustration, and not limitation, nonvolatile memory 922 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 920 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 912 also includes removable/non-removable, volatile/non-volatile computer storage media. FIG. 9 illustrates, for example, a disk storage 924. Disk storage 924 includes, but is not limited to, devices like a magnetic disk drive, floppy disk drive, tape drive, Jaz drive, Zip drive, LS-100 drive, flash memory card, or memory stick. The disk storage 924 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 924 to the system bus 918, a removable or non-removable interface is typically used, such as interface 926.

FIG. 9 also depicts software that acts as an intermediary between users and the basic computer resources described in the suitable operating environment 900. Such software includes, for example, an operating system 928. Operating system 928, which can be stored on disk storage 924, acts to control and allocate resources of the computer system 912. System applications 930 take advantage of the management of resources by operating system 928 through program modules 932 and program data 934, e.g., stored either in system memory 916 or on disk storage 924. It is to be appreciated that this disclosure can be implemented with various operating systems or combinations of operating systems.

A user enters commands or information into the computer 912 through input device(s) 936. Input devices 936 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 914 through the system bus 918 via interface port(s) 938. Interface port(s) 938 include, for example, a serial port, a parallel port, a game port, and a universal serial bus (USB). Output device(s) 940 use some of the same type of ports as input device(s) 936. Thus, for example, a USB port may be used to provide input to computer 912, and to output information from computer 912 to an output device 940. Output adapter 942 is provided to illustrate that there are some output devices 940 like monitors, speakers, and printers, among other output devices 940, which require special adapters. The output adapters 942 include, by way of illustration and not limitation, video and sound cards that provide a means of connection between the output device 940 and the system bus 918. It should be noted that other devices and/or systems of devices provide both input and output capabilities such as remote computer(s) 944.

Computer 912 can operate in a networked environment using logical connections to one or more remote computers, such as remote computer(s) 944. The remote computer(s) 944 can be a personal computer, a server, a router, a network PC, a workstation, a microprocessor based appliance, a peer device or other common network node and the like, and typically includes many or all of the elements described relative to computer 912. For purposes of brevity, only a memory storage device 946 is illustrated with remote computer(s) 944. Remote computer(s) 944 is logically connected to computer 912 through a network interface 948 and then physically connected via communication connection 950. Network interface 948 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 950 refers to the hardware/software employed to connect the network interface 948 to the bus 918. While communication connection 950 is shown for illustrative clarity inside computer 912, it can also be external to computer 912. The hardware/software necessary for connection to the network interface 948 includes, for exemplary purposes only, internal and external technologies such as, modems including regular telephone grade modems, cable modems and DSL modems, ISDN adapters, and Ethernet cards.

FIG. 10 is a schematic block diagram of a sample-computing environment 1000 with which the subject matter of this disclosure can interact. The system 1000 includes one or more client(s) 1010. The client(s) 1010 can be hardware and/or software (e.g., threads, processes, computing devices). The system 1000 also includes one or more server(s) 1030. Thus, system 1000 can correspond to a two-tier client server model or a multi-tier model (e.g., client, middle tier server, data server), amongst other models. The server(s) 1030 can also be hardware and/or software (e.g., threads, processes, computing devices). The servers 1030 can house threads to perform transformations by employing this disclosure, for example. One possible communication between a client 1010 and a server 1030 may be in the form of a data packet transmitted between two or more computer processes.

The system 1000 includes a communication framework 1050 that can be employed to facilitate communications between the client(s) 1010 and the server(s) 1030. The client(s) 1010 are operatively connected to one or more client data store(s) 1020 that can be employed to store information local to the client(s) 1010. Similarly, the server(s) 1030 are operatively connected to one or more server data store(s) 1040 that can be employed to store information local to the servers 1030.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A machine learning system, comprising:
    a memory that stores computer executable components; and
    a processor that executes the computer executable components stored in the memory, wherein the computer executable components comprise:
        an atlas map component that generates atlas map data indicative of an atlas map that includes a set of normal patient image data for a plurality of first pediatric patients and a set of abnormal patient image data for a plurality of second pediatric patients, different from the plurality of first pediatric patients, wherein the set of normal patient image data and the set of abnormal patient image data are respective pediatric brain scan images, and wherein normal patient image data of the set of normal patient image data and abnormal patient image data of the set of abnormal patient image data is assigned to respective pediatric age groups based on respective patient identities;
        a deviation map component that converts numerical data values included in the atlas map data into data values formatted based on a first amount of deviation of the set of abnormal patient image data compared to the set of normal patient image data and generates, based on the data values, deviation map data that represents a second amount of deviation for the set of abnormal patient image data compared to the normal patient image data; and
        a neural network component that trains a neural network based on the deviation map data to determine respective clinical conditions for another set of patient image data of a plurality of third pediatric patients, different from the plurality of first pediatric patients and the plurality of second pediatric patients.

2. The machine learning system of claim 1, wherein the atlas map component generates a statistical representation of the set of normal patient image data.

3. The machine learning system of claim 1, wherein the atlas map component generates an image intensity value associated with a mean value and a standard deviation value for a data value in the atlas map.

4. The machine learning system of claim 3, wherein the deviation map component subtracts the mean value from the image intensity value to generate a difference value, and divides the difference value by the standard deviation value to facilitate generation of the deviation map data.

5. The machine learning system of claim 1, wherein the atlas map component configures a first portion of the atlas map data as a set of age-matched groupings associated with the set of normal patient image data, and wherein the atlas map component configures a second portion of the atlas map data as a set of abnormal medical condition groupings associated with the set of abnormal patient image data.

6. The machine learning system of claim 1, wherein the atlas map component normalizes the set of normal patient image data and the abnormal patient image data to generate the atlas map data.

7. The machine learning system of claim 1, wherein the atlas map component formats the atlas map data as a matrix of numerical data values that represent the set of normal patient image data and the set of abnormal patient image data.

8. The machine learning system of claim 7, wherein the deviation map component converts the matrix of numerical data values into a matrix of colorized data values formatted based on the second amount of deviation for the set of abnormal patient image data compared to the set of normal patient image data, wherein a first colorized data value of the matrix of colorized data values corresponds to a normal medical condition, wherein a second colorized data value of the matrix of colorized data values corresponds to a possible abnormal medical condition, and wherein a third colorized data value of the matrix of colorized data values corresponds to an abnormal medical condition.

9. The machine learning system of claim 1, where the neural network performs a plurality of sequential and/or parallel downsampling and upsampling of the deviation map data associated with convolutional layers of the neural network.

10. A method, comprising using a processor operatively coupled to memory to execute computer executable components to perform the following acts:
    generating atlas map data indicative of an atlas map that includes a set of normal patient image data for a plurality of first pediatric patients and a set of abnormal patient image data for a plurality of second pediatric patients that exhibit respective clinical conditions, wherein the set of normal patient image data is matched to respective pediatric age groups for respective patient identities associated with the set of normal patient image data and the set of abnormal patient image data;
    generating deviation map data that represents an amount of deviation between the set of abnormal patient image data and the set of normal patient image data, wherein the deviation map data comprises multi-dimensional visualization data that represent one or more predicted locations for a disease associated with the set of abnormal patient image data, and wherein respective visual characteristics of the multi-dimensional visualization data represent different degrees of likelihood for the disease associated with the set of abnormal patient image data; and training a neural network based on the deviation map data to determine one or more clinical conditions associated with respective patient image data of another set of patient image data associated with at least a third pediatric patient, wherein the set of normal patient image data, the set of abnormal patient image data, and another set of patient image data are respective pediatric brain scan images.

11. The method of claim 10, wherein the generating the atlas map data comprises grouping the set of normal patient image data based on a set of age groups for the respective patient identities.

12. The method of claim 10, wherein the generating the atlas map data comprises configuring a portion of the atlas map data as a set of age-matched groupings associated with the set of normal patient image data.

13. The method of claim 10, wherein the generating the atlas map data comprises configuring a portion of the atlas map data as a set of abnormal medical condition groupings associated with the set of abnormal patient image data.

14. The method of claim 10, wherein the generating the atlas map data comprises normalizing the set of normal patient image data and the set of abnormal patient image data to generate the atlas map data.

15. The method of claim 10, wherein the generating the atlas map data comprises formatting the atlas map data as a matrix of numerical data values that represent the set of normal patient image data and the set of abnormal patient image data.

16. The method of claim 15, wherein the generating deviation map data comprises converting the matrix of numerical data values into a matrix of colorized data values formatted based on the amount of deviation for the set of abnormal patient image data compared to the set of normal patient image data.

17. A non-transitory computer readable storage device comprising instructions that, in response to execution, cause a system comprising a processor to perform operations, comprising:
generating atlas map data indicative of an atlas map that includes a group of normal patient image data for a first set of pediatric patients and a group of abnormal patient image data of a plurality of clinical conditions for a second set of pediatric patients, different from the first set of pediatric patients, wherein the group of normal patient image data is matched to a corresponding age group for a first set of patient identities associated with the group of normal patient image data, and wherein the group of abnormal patient image data is matched to the corresponding age group for a second set of patient identities associated with the group of abnormal patient image data;
modifying the atlas map data to generate deviation map data that represents an amount of deviation between the group of abnormal patient image data and the group of normal patient image data; and
training a neural network to classify one or more clinical conditions associated with respective patient image data of another set of patient image data of a third set of pediatric patients based on the deviation map data, wherein classification of the one or more clinical conditions is not based on the patient image data.

18. The non-transitory computer readable storage device of claim 17, wherein the generating the atlas map data comprises normalizing the group of normal patient image data and the group of abnormal patient image data.

19. The non-transitory computer readable storage device of claim 17, wherein the generating the atlas map data comprises formatting the atlas map data as a matrix of numerical data values that represent the group of normal patient image data and the group of abnormal patient image data.

20. The non-transitory computer readable storage device of claim 19, wherein the modifying the atlas map data comprises converting the matrix of numerical data values into a matrix of colorized data values formatted based on the amount of deviation for the group of abnormal patient image data compared to the group of normal patient image data.

* * * * *